(12) United States Patent
Zitting et al.

(10) Patent No.: US 9,943,249 B2
(45) Date of Patent: Apr. 17, 2018

(54) RESPIRATORY GAS MONITOR TESTING SYSTEM AND METHODS OF USE

(71) Applicants: Darryl Zitting, Washington, UT (US); Joseph A. Orr, Park City, UT (US); Brent Weight, St. George, UT (US)

(72) Inventors: Darryl Zitting, Washington, UT (US); Joseph A. Orr, Park City, UT (US); Brent Weight, St. George, UT (US)

(*) Notice: Subject to any disclaimer, the term of this patent is extended or adjusted under 35 U.S.C. 154(b) by 147 days.

(21) Appl. No.: 15/210,773

(22) Filed: Jul. 14, 2016

(65) Prior Publication Data
US 2017/0016799 A1 Jan. 19, 2017

Related U.S. Application Data

(60) Provisional application No. 62/192,313, filed on Jul. 14, 2015.

(51) Int. Cl.
*A61M 16/00* (2006.01)
*A62B 7/00* (2006.01)
(Continued)

(52) U.S. Cl.
CPC ............... *A61B 5/082* (2013.01); *G01M 3/26* (2013.01); *G09B 23/288* (2013.01);
(Continued)

(58) Field of Classification Search
CPC ... A61B 5/08; A61B 5/082; A61B 2560/0223; A61B 2560/0276; A61M 16/00;
(Continued)

(56) References Cited

U.S. PATENT DOCUMENTS 8,986,216 B2 * 3/2015 Unger .................... A62B 27/00
600/529
2011/0259330 A1 * 10/2011 Jafari .................. A61M 16/024
128/204.18
(Continued)

FOREIGN PATENT DOCUMENTS

EP 1961439 A1 * 8/2008 ........ A61M 16/0051
GB 1451878 A * 10/1976 ............. A61B 5/087
(Continued)

*Primary Examiner* — Nguyen Ha
(74) *Attorney, Agent, or Firm* — Gallian, Welker & Beckstrom, L.C.; Robert A. Gurr

(57) ABSTRACT

A respiratory gas monitor testing system having a respiratory gas monitor coupled to a system for detecting a leak, wherein the system for detecting a leak has a flowmeter in fluid communication with both an inlet and an outlet of the respiratory gas monitor, with the exhaust of the flowmeter venting to atmosphere; a restriction valve, a sample pressure sensor, a flowmeter valve configured to allow the flowmeter to either measure sample flow rate or leak rate, a flow-smoothing buffer configured to improve flow measurement accuracy, and a system for simulating human breath; wherein the system for simulating human breath at elevated airway pressure has an air source, a calibration gas source, a breath simulation valve, a calibration gas valve, a sample pressure sensor, an air reservoir, a pressurized bottle with a pressure regulator and an orifice, and an air pump.

23 Claims, 16 Drawing Sheets

(51) Int. Cl.
*A62B 9/00* (2006.01)
*G01M 3/26* (2006.01)
*G09B 23/28* (2006.01)
*A61B 5/08* (2006.01)
*A61M 16/10* (2006.01)

(52) U.S. Cl.
CPC ......... *A61B 2560/0223* (2013.01); *A61B 2560/0276* (2013.01); *A61M 16/0051* (2013.01); *A61M 16/022* (2017.08); *A61M 16/1005* (2014.02); *A61M 2016/1035* (2013.01); *A61M 2205/15* (2013.01); *A61M 2209/02* (2013.01); *A62B 9/003* (2013.01)

(58) Field of Classification Search
CPC ......... A61M 16/0051; A61M 16/022; A61M 2205/15; A61M 2209/02; A61M 16/1005; A61M 16/1035; G01M 3/00; G01M 3/26; G09B 23/28; G09B 23/288; A62B 9/00; A62B 9/003; A62B 97/00
See application file for complete search history.

(56) References Cited

U.S. PATENT DOCUMENTS

| | | | |
|---|---|---|---|
| 2012/0065533 A1* | 3/2012 | Carrillo, Jr. | A61B 5/083 600/532 |
| 2015/0273172 A1* | 10/2015 | Pessala | A61M 16/0051 128/203.12 |
| 2016/0370213 A1* | 12/2016 | Stromsten | G01F 1/40 |

FOREIGN PATENT DOCUMENTS

| | | | | |
|---|---|---|---|---|
| JP | 2017148550 A | * | 8/2017 | ........ A61M 16/0051 |
| WO | WO 2014068000 A1 | * | 5/2014 | ........ A61M 16/0051 |

* cited by examiner

| Smart Tank Diagnostic Logic | | | | |
|---|---|---|---|---|
| Test Results: | Sample flow rate out of spec | Sample flow rate out of spec (leak may be cause) | Sample flow rate out of spec (downstream leak can't be cause) | Sample flow rate out of spec (leak may be cause - no exh line) |
| Sample flow rate in spec at ambient pressure? | FAIL | FAIL | FAIL | FAIL |
| No leak at ambient pressure? | PASS | FAIL | FAIL | |
| Baseline leak value is negative? | | PASS | FAIL | |
| Sample flow not significantly lower under neg pressure load than at ambient? | | | | |
| No leak under neg pressure load? | | | | |
| Leak at challange pressure is no larger than at baseline? | | | | |
| EtCO2 accurate at ambient pressure? | | | | |
| EtCO2 not higher with static positive pressure than at ambient pressure? | PASS | | | FAIL |
| EtCO2 is not higher or lower with static pos pressure than at ambient pressure? | | | | |
| EtCO2 accurate at max RR? | | | | |
| Apnea alarm functional? | | | | |
| Occlusion alarm functional? | | | | |
| Is the RGMs exhaust port connected? | | PASS | PASS | FAIL |
| Diagnostic messages: ----->> | Sample flow rate is out of spec. | Sample flow rate is out of spec. The leak that was detected may have caused this parameter to fail. Eliminate the leak then re-run the test. | Sample flow rate is out of spec. The leak that was detected most likely did not cause this parameter to fail. | Sample flow rate is out of spec. The leak that was detected may have caused this parameter to fail. Eliminate the leak then re-run the test. |

FIG. 5A

| Smart Tank Diagnostic Logic | | | | |
|---|---|---|---|---|
| Test Results: | Sample pump defect | Sample pump defect (leak may be cause) | Sample pump defect (downstream leak can't be cause) | Sample pump defect (leak may be cause - no exh line) |
| Sample flow rate in spec at ambient pressure? | | | | |
| No leak at ambient pressure? | PASS | FAIL_OR | FAIL | |
| Baseline leak value is negative? | | PASS | FAIL | |
| Sample flow not significantly lower under neg pressure load than at ambient? | FAIL | FAIL | FAIL | FAIL |
| No leak under neg pressure load? | PASS | FAIL_OR | | |
| Leak at challange pressure is no larger than at baseline? | | | | |
| EtCO2 accurate at ambient pressure? | | | | |
| EtCO2 not higher with static positive pressure than at ambient pressure? | | | | FAIL |
| EtCO2 is not higher or lower with static pos pressure than at ambient pressure? | | | | |
| EtCO2 accurate at max RR? | | | | |
| Apnea alarm functional? | | | | |
| Occlusion alarm functional? | | | | |
| Is the RGMs exhaust port connected? | PASS | PASS | PASS | FAIL |
| Diagnostic messages: ----->> | Sample pump weakness detected. No leaks were detected, but the sample flow rate dropped too much when challanged. | Sample pump weakness detected. The leak that was detected may have caused this parameter to fail. Eliminate the leak then re-run the test. | Sample pump weakness detected. The leak that was detected most likeley did not cause this parameter to fail. | Sample pump weakness detected. The leak that was detected may have caused this parameter to fail. Eliminate the leak then re-run the test. |

FIG. 5B

| Smart Tank Diagnostic Logic Test Results: | Leak upstream of sensor | Leak most likely between sensor and pump | Leak downstream of pump | Possible leak detected without exhaust line | Leak only at neg. pressure |
|---|---|---|---|---|---|
| Sample flow rate in spec at ambient pressure? | | | | | |
| No leak at ambient pressure? | FAIL_OR | FAIL | FAIL | | PASS |
| Baseline leak value is negative? | PASS | PASS | FAIL | | |
| Sample flow not significantly lower under neg pressure load than at ambient? | | | | | |
| No leak under neg pressure load? | FAIL_OR | FAIL | | | FAIL |
| Leak at challange pressure is no larger than at baseline? | | FAIL | | | |
| EtCO2 accurate at ambient pressure? | | | | | |
| EtCO2 not higher with static positive pressure than at ambient pressure? | FAIL | PASS | | FAIL | |
| EtCO2 is not higher or lower with static pos pressure than at ambient pressure? | | | | | |
| EtCO2 accurate at max RR? | | | | | |
| Apnea alarm functional? | | | | | |
| Occlusion alarm functional? | | | | | |
| Is the RGMs exhaust port connected? | PASS | PASS | PASS | FAIL | PASS |
| Diagnostic messages: ------>> | Leak detected upstream of sensor. The effect of a leak that occurs at ambient pressure is generally calibrated out, but when sample pressure changes (i.e, mechanical ventilation), the leak rate changes so the leak again affects the reading. | Leak detected. Leak location is most likely between the sensor and pump. Leaks downstream of the sensor may not have any effect on the RGMs performance. | Leak detected downstream of pump. Leaks downstream of the pump may not have any effect on the RGMs performance. | There may be a leak upstream of the sensor. Because the RGMs exhaust line was not connected, we could not directly measure the leak to verify. | A leak was detected that only occurs at more negative sample pressure (as in the case when a longer sampling line is employed). This may be caused by a defective zeroing valve. |

FIG. 5C

| Smart Tank Diagnostic Logic | | | |
|---|---|---|---|
| Test Results: | Gas sensor response time out of spec | Gas sensor response time out of spec. (leak may be cause) | Gas sensor response time out of spec. (downstream leak can't be cause) |
| Sample flow rate in spec at ambient pressure? | PASS | | |
| No leak at ambient pressure? | PASS | FAIL | FAIL |
| Baseline leak value is negative? | | PASS | FAIL |
| Sample flow not significantly lower under neg pressure load than at ambient? | | | |
| No leak under neg pressure load? | | | |
| Leak at challange pressure is no larger than at baseline? | | | |
| EtCO2 accurate at ambient pressure? | | | |
| EtCO2 not higher with static positive pressure than at ambient pressure? | | | |
| EtCO2 is not higher or lower with static pos pressure than at ambient pressure? | | | |
| EtCO2 accurate at max RR? | FAIL | FAIL | FAIL |
| Apnea alarm functional? | | | |
| Occlusion alarm functional? | | | |
| Is the RGMs exhaust port connected? | PASS | PASS | PASS |
| Diagnostic messages: ----->> | Gas sensor response time out of spec. Response time failure may be caused by: Incorrect sample line, water in the system, defective water trap or anything that causes mixing of the sample before it reaches the sensor. | Gas sensor response time out of spec. The leak that was detected may have caused this parameter to fail. Eliminate the leak then re-run the test. | Gas sensor response time out of spec. The leak detected most likely did not cause this parameter to fail. Response time failure may be caused by: Incorrect sample line, water in the system, defective water trap or anything that causes mixing of the sample before it reaches the sensor. |

FIG. 5D

Smart Tank Diagnostic Logic

| Test Results: | Gas sensor response time out of spec - no exh line | Gas sensor response time out of spec. (leak may be cause - no exh line) | Gas sensor response time out of spec. (sample flow may be cause) |
|---|---|---|---|
| Sample flow rate in spec at ambient pressure? | PASS | | FAIL |
| No leak at ambient pressure? | | | |
| Baseline leak value is negative? | | | |
| Sample flow not significantly lower under neg pressure load than at ambient? | | | |
| No leak under neg pressure load? | | | |
| Leak at challange pressure is no larger than at baseline? | | | |
| EtCO2 accurate at ambient pressure? | | | |
| EtCO2 not higher with static positive pressure than at ambient pressure? | PASS | FAIL | |
| EtCO2 is not higher or lower with static pos pressure than at ambient pressure? | | | |
| EtCO2 accurate at max RR? | FAIL | FAIL | FAIL |
| Apnea alarm functional? | | | |
| Occlusion alarm functional? | FAIL | FAIL | |
| Is the RGMs exhaust port connected? | | | |
| Diagnostic messages: ----->> | Gas sensor response time out of spec. Response time failure may be caused by: Incorrect sample line, water in the system, defective water trap or anything that causes mixing of the sample before it reaches the sensor. | Gas sensor response time out of spec. The leak that was detected may have caused this parameter to fail. Eliminate the leak then re-run the test. | Gas sensor response time out of spec. The out of spec sample flow rate may have caused this parameter to fail. Calibrate the sample flow rate then re-run the test. |

FIG. 5E

| Smart Tank Diagnostic Logic Test Results: | EtCO2 inaccurate (no leak, sample rate good) | EtCO2 inaccurate - no exh line | EtCO2 inaccurate (downstream leak and mis-cal) | EtCO2 inaccurate (leak may be cause) | EtCO2 inaccurate (leak may be cause - no exh line) | EtCO2 inaccurate (flow rate may be cause) |
|---|---|---|---|---|---|---|
| Sample flow rate in spec at ambient pressure? | PASS | PASS | PASS | | | FAIL |
| No leak at ambient pressure? | PASS | | FAIL | FAIL | | |
| Baseline leak value is negative? | | | FAIL | PASS | | |
| Sample flow not significantly lower under neg pressure load than at ambient? | | | | | | |
| No leak under neg pressure load? | | | | | | |
| Leak at challange pressure is no larger than at baseline? | | | | | | |
| EtCO2 accurate at ambient pressure? | FAIL | FAIL | FAIL | FAIL | FAIL | FAIL |
| EtCO2 not higher with static positive pressure than at ambient pressure? | | PASS | | | FAIL | |
| EtCO2 is not higher or lower with static pos pressure than at ambient pressure? | | | | | | |
| EtCO2 accurate at max RR? | | | | | | |
| Apnea alarm functional? | | | | | | |
| Occlusion alarm functional? | | | | | | |
| Is the RGMs exhaust port connected? | PASS | FAIL | PASS | PASS | FAIL | |
| Diagnostic messages: ----->> | Gas sensor reading is out of spec. Calibrate sensor and re-run the test | Gas sensor reading is out of spec. Calibrate sensor and re-run the test | Gas sensor reading is out of spec. The leak detected most likely did not cause this result. Calibrate sensor and re-run the test. | Gas sensor may require calibration. The leak that was detected may have caused this parameter to fail. Eliminate the leak then re-run the test. | Gas sensor may require calibration. The leak that was detected may have caused this parameter to fail. Eliminate the leak then re-run the test. | Gas sensor may require calibration. The out of spec sample flow rate may have caused this parameter to fail. Calibrate the sample flow rate then re-run the test. |

FIG. 5F

| Smart Tank Diagnostic Logic | |
|---|---|
| Test Results: | Pressure comp. function defect |
| Sample flow rate in spec at ambient pressure? | |
| No leak at ambient pressure? | PASS |
| Baseline leak value is negative? | |
| Sample flow not significantly lower under neg pressure load than at ambient? | PASS |
| No leak under neg pressure load? | |
| Leak at challange pressure is no larger than at baseline? | |
| EtCO2 accurate at ambient pressure? | |
| EtCO2 not higher with static positive pressure than at ambient pressure? | |
| EtCO2 is not higher or lower with static pos pressure than at ambient pressure? | FAIL |
| EtCO2 accurate at max RR? | |
| Apnea alarm functional? | |
| Occlusion alarm functional? | |
| Is the RGMs exhaust port connected? | PASS |
| Diagnostic messages: ——>> | Pressure compensation function may be malfunctioning. EtCO2 accuracy was affected by the sample pressure (i.e. mechanical ventialtion) even though no leak was detected. |

FIG. 5G

| Smart Tank Diagnostic Logic | |
|---|---|
| Test Results: | Apnea alarm malf. |
| Sample flow rate in spec at ambient pressure? | |
| No leak at ambient pressure? | |
| Baseline leak value is negative? | |
| Sample flow not significantly lower under neg pressure load than at ambient? | |
| No leak under neg pressure load? | |
| Leak at challange pressure is no larger than at baseline? | |
| EtCO2 accurate at ambient pressure? | |
| EtCO2 not higher with static positive pressure than at ambient pressure? | |
| EtCO2 is not higher or lower with static pos pressure than at ambient pressure? | |
| EtCO2 accurate at max RR? | |
| Apnea alarm functional? | FAIL |
| Occlusion alarm functional? | |
| Is the RGMs exhaust port connected? | |
| Diagnostic messages: ----->> | Apnea alarm malfunction. |

FIG. 5H

| Smart Tank Diagnostic Logic | | | | |
|---|---|---|---|---|
| Test Results: | Occlusion alarm malf. | Occlusion alarm malf. (leak may be cause) | Occlusion alarm malf. (downstream leak can't be cause) | Occlusion alarm malf. (leak may be cause - no exh line) |
| Sample flow rate in spec at ambient pressure? | | | | |
| No leak at ambient pressure? | PASS | | FAIL | |
| Baseline leak value is negative? | | PASS | FAIL | |
| Sample flow not significantly lower under neg pressure load than at ambient? | | | | |
| No leak under neg pressure load? | PASS | FAIL | | |
| Leak at challange pressure is no larger than at baseline? | | | | |
| EtCO2 accurate at ambient pressure? | | | | |
| EtCO2 not higher with static positive pressure than at ambient pressure? | | | | FAIL |
| EtCO2 is not higher or lower with static pos pressure than at ambient pressure? | | | | |
| EtCO2 accurate at max RR? | | | | |
| Apnea alarm functional? | | | | |
| Occlusion alarm functional? | FAIL | FAIL | FAIL | FAIL |
| Is the RGMs exhaust port connected? | PASS | PASS | PASS | FAIL |
| Diagnostic messages: ----->> | Occlusion alarm malfunction. | Occlusion alarm malfunction. The leak that was detected may have caused this parameter to fail. Eliminate the leak then re-run the test. | Occlusion alarm malfunction. The leak that was detected most likely did not cause this parameter to fail. | Occlusion alarm malfunction. The leak that was detected may have caused this parameter to fail. Eliminate the leak then re-run the test. |

FIG. 51

RESPIRATORY GAS MONITOR TESTING SYSTEM AND METHODS OF USE

CROSS-REFERENCE TO RELATED APPLICATIONS

This application claims the benefit of the U.S. Provisional Application Ser. No. 62/192,313, filed on Jul. 14, 2015, which is incorporated herein by reference.

TECHNICAL FIELD

The present disclosure relates generally to health monitoring devices and methods for testing the same. More particularly, the present disclosure relates to devices for testing patient gas monitors, such as capnometers and anesthesia gas analyzers, and methods of simulating patient breathing for use with the same.

BACKGROUND

Two out of three unexpected hospital deaths are attributed to hypoventilation, many of which could be prevented if hypoventilation is detected earlier. During hypoventilation, as the concentration of carbon dioxide ($CO_2$) in the patient's arterial blood rises (hypercarbia), the patient becomes increasingly susceptible to abnormal cardiac rhythms and, ultimately, cardiac arrest and death. Capnometers and pulse oximeters form the front-line safety net for detecting hypoventilation when patients have compromised gas exchange during procedural sedation, anesthesia or cardiopulmonary illness. When supplemental oxygen is being delivered, oximeters are less effective leaving capnometers to provide the only reliable real-time warning of potentially fatal hypoventilation. Thus, it is imperative that capnometers function correctly to ensure patient safety. Unfortunately, one out of every hundred incidence reports involving capnometry misreading is attributed to capnometer malfunction. These incidences could have been avoided if the functional issues had been properly detected in a timely manner.

For nearly all clinical monitors (ECG, blood pressure, etc.), clinical engineers use patient simulation devices to create precise, clinically realistic, signals against which the parameters reported by the monitor are compared. At present, there is no such patient simulation device for capnometers and anesthetic agent analyzers (a.k.a: respiratory gas monitors, or "RGMs"). RGMs function by drawing a sample of exhaled/inhaled gas from the patient's airway through tubing to the gas monitor sample inlet port, analyzing the sample inside the RGM, and then venting the analyzed sample through an exhaust port. Within a typical RGM is a sampling pump that creates negative pressure to draw the sample to the monitor through the sampling tube. Also within the RGM are valves, tubing, chambers, etc. which have the tendency to develop leaks or other malfunctions. Most of these components are typically on the sampling side (negative pressure side) of the sampling pump. Even very small leaks in the sampling gas pathway can cause ambient air to be drawn in and mixed with the sample gas, resulting in a diluted sample and, therefore, an inaccurate measurement. These leaks can be very difficult to detect, because their effect is typically calibrated out during routine calibration. However, the magnitude and effect of the leak changes with sample inlet pressure, so a monitor that appears to work normally during calibration may read inaccurately when put into use and subjected to changing pressures, such as those encountered during mechanical ventilation. As such, there are many capnometer failure modes that can only be detected under dynamic pressure and $CO_2$ levels experienced during real patient use. Capnometer performance is currently verified using a static flow of calibration gas at ambient pressure, which is incapable of detecting failure modes that only exhibit in real-world conditions.

Given the foregoing, there is a need for a reliable gas monitor leak detection device, as well as a patient simulator that can simulate patient breath at pressures common during mechanical ventilation. Such a system will allow for the detection of additional failure modes that are currently undetectable by traditional test methods. The current disclosure seeks to solve these and other problems.

SUMMARY OF EXAMPLE EMBODIMENTS

In one embodiment, a respiratory gas monitor testing system comprises a respiratory gas monitor coupled to a system for detecting a leak, wherein the system for detecting a leak comprises a flowmeter in fluid communication with both an inlet and an outlet of the respiratory gas monitor, with the exhaust of the flowmeter venting to atmosphere.

In one embodiment, a method of using a respiratory gas monitor testing system to determine a leak rate comprises creating a gas flow loop by placing an inlet of a gas monitor in fluid communication with the exhaust of the gas monitor, connecting an inlet of a flowmeter to the gas flow loop and allowing the exhaust of the flowmeter to vent to atmosphere, and monitoring the flow of gas in or out of the vent through the flowmeter.

A respiratory gas monitor testing system, comprising a system of simulating patient breath, comprising inputting calibration gas through a pressure regulator and to a breath valve; the breath valve configured to alternate between an open and closed state; wherein if the breath valve is open, the calibration gas flows to a respiratory gas monitor; a vent positioned between the breath valve and the respiratory gas monitor such that excess gas flow from the breath valve that is not drawn in by the respiratory gas monitor will be vented to atmosphere; and wherein if the breath valve is closed, the calibration gas flow is stopped and ambient air enters from an air source, the ambient air flowing to the respiratory gas monitor.

A system of determining proper functionality of a respiratory gas monitor using a method of simulating patient breath, comprising comparing the composition of gas in the ambient air and the composition of gas in a calibration gas source, corrected for barometric pressure, with the respiratory parameters output by the respiratory gas monitor.

In one embodiment, a method of using a respiratory gas monitor testing system to determine a leak rate in a diverting gas monitor comprises measuring the inlet flow rate of the diverting gas monitor, measuring the exhaust flow rate of the diverting gas monitor, and determining the difference in rates to derive the leak rate.

In one embodiment, a method of using a respiratory gas monitor testing system for detecting sensor response time comprises alternating the gas levels being delivered to a gas monitor, wherein the frequency of the alternation increases over time, and monitoring the end-tidal value displayed by the RGM during ascending respiratory rate. As the rate increases, the sensor will fail to transition fast enough, and will instead begin to read a mixture of the two gasses. When a mixed reading given by the RGM falls outside of the manufacturer stated accuracy specification, the response time is then known.

In yet another embodiment, a method of using a respiratory gas monitor testing system for conserving expensive calibration gas comprises measuring the sample flow rate of the RGM and delivering slightly more calibration gas flow than is required by the RGM.

In one embodiment, a respiratory gas monitor testing system comprises a system of simulating patient breath and a system for detecting a leak.

A method of using a respiratory gas monitor testing system to diagnose a malfunction of a respiratory gas monitor, comprising the steps of (a) coupling the respiratory gas monitor to the respiratory gas monitor testing system, wherein the respiratory gas monitor testing system comprises the logic as described in Table 5A-5I; and (b) diagnosing the malfunction of the respiratory gas monitor according to the logic.

DETAILED DESCRIPTION OF EXAMPLE EMBODIMENT(S)

Figure 1A:
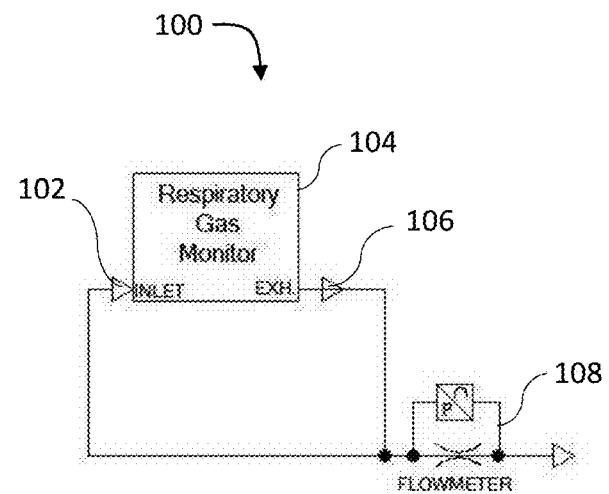
FIG. 1A is a pneumatic schematic of a system for detecting leaks in a RGM.

The following descriptions depict only example embodiments and are not to be considered limiting of its scope. Any reference herein to "the invention" is not intended to restrict or limit the invention to exact features or steps of any one or more of the exemplary embodiments disclosed in the present specification. References to "one embodiment," "an embodiment," "various embodiments," and the like, may indicate that the embodiment(s) so described may include a particular feature, structure, or characteristic, but not every embodiment necessarily includes the particular feature, structure, or characteristic. Further, repeated use of the phrase "in one embodiment," or "in an embodiment," do not necessarily refer to the same embodiment, although they may.

Reference to any included drawings is done throughout the disclosure using various numbers. The numbers used are for the convenience of the drafter only and the absence of numbers in an apparent sequence should not be considered limiting and does not imply that additional parts of that particular embodiment exist. Numbering patterns from one embodiment to the other need not imply that each embodiment has similar parts, although it may.

Accordingly, the particular arrangements disclosed are meant to be illustrative only and not limiting as to the scope of the invention. Although specific terms are employed herein, they are used in a generic and descriptive sense only and not for purposes of limitation. Unless otherwise expressly defined herein, such terms are intended to be given their broad, ordinary, and customary meaning not inconsistent with that applicable in the relevant industry and without restriction to any specific embodiment hereinafter described. As used herein, the article "a" is intended to include one or more items. When used herein to join a list of items, the term "or" denotes at least one of the items, but does not exclude a plurality of items of the list. For exemplary methods or processes, the sequence and/or arrangement of steps described herein are illustrative and not restrictive.

It should be understood that the steps of any such processes or methods are not limited to being carried out in any particular sequence, arrangement, or with any particular graphics or interface. Indeed, the steps of the disclosed processes or methods generally may be carried out in various different sequences and arrangements while still falling within the scope of the present invention.

The term "coupled" may mean that two or more elements are in direct physical or electrical contact. However, "coupled" may also mean that two or more elements are not in direct contact with each other, but yet still cooperate or interact with each other.

The terms "comprising," "including," "having," and the like, as used with respect to embodiments, are synonymous, and are generally intended as "open" terms (e.g., the term "including" should be interpreted as "including but not limited to," the term "having" should be interpreted as "having at least," the term "includes" should be interpreted as "includes but is not limited to," etc.).

Further, it will be appreciated that while "capnometers" are used as an example device throughout the disclosure, other apparatuses are contemplated, such as anesthesia gas analyzers or any other sample diverting gas monitor known in the art.

In one embodiment, as shown in FIG. 1A, a system for detecting a leak rate, generally shown at 100, in a respiratory gas monitor, comprises creating a gas flow loop by placing the inlet 102 of a gas monitor 104 in fluid communication with the exhaust 106 of the gas monitor 104. The loop further comprises a flowmeter 108 with one port in fluid communication with the loop and the other port left open to the ambient air. Due to conservation of mass, any leak in the gas monitor 104 will cause an equal volume to flow through the flowmeter 108. This allows for direct measurement of the leak rate.

Figure 1B:
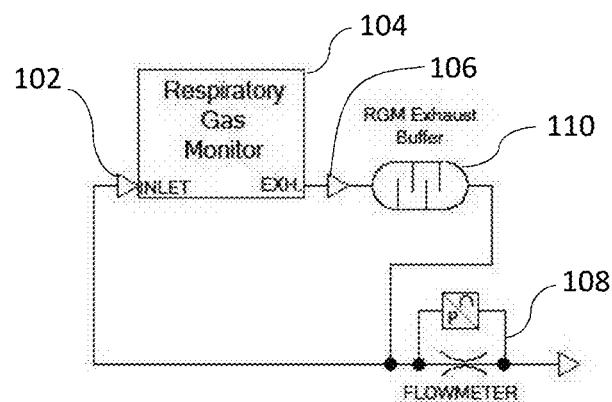
FIG. 1B is a pneumatic schematic of a system for detecting leaks comprising a buffer to smooth the flow of gas exiting the RGM.

In one embodiment, as shown in FIG. 1B, a buffer chamber 110 may also be coupled to the gas loop to smooth the flow of gas exiting the RGM. This may be desirable when the sample pump in the gas monitor 104 is a diaphragm style, which results in a pulsatile flow exiting the gas monitor 104, causing inaccuracy in flow measurement readings.

Figure 1C:
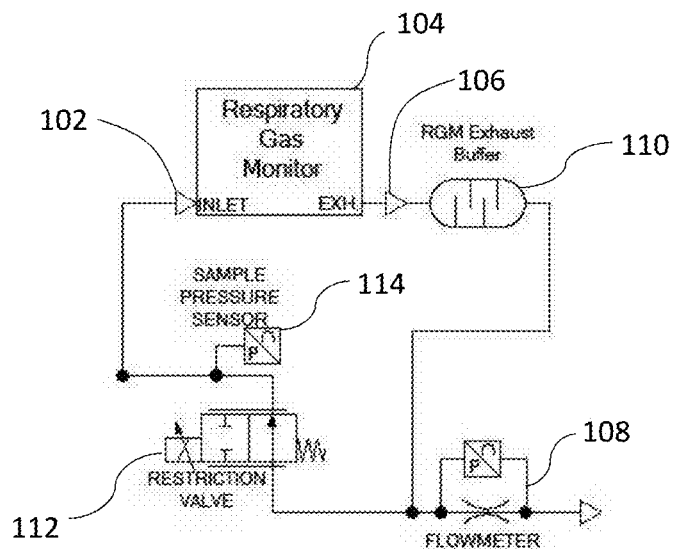
FIG. 1C is a pneumatic schematic of a system for detecting leaks comprising a restriction valve to challenge the RGM sampling system during leak measurement.

In another embodiment, as shown in FIG. 1C, a system of detecting the leak rate may also comprise a restriction valve 112 and a sample pressure sensor 114. Most gas monitors are designed to increase the sample pump rate, if the sampling line becomes restricted or occluded, in an effort to maintain a constant flow rate of gas through the system. If the length of the sample line is increased, or humidity or other particle/material enters the sample line, the monitor will compensate, resulting in a more negative pressure in the sampling line. Some leaks may only occur at greater negative pressures. As such, the restriction valve 112 may restrict the flow of gas in order to target a particular negative pressure level during the leak test to detect leaks that only occur at greater negative pressure. This also allows the system to measure the sample flow with flow restriction to determine if the RGM is correctly maintaining the correct sample flow rate at more negative sample line pressures.

Figure 1D:
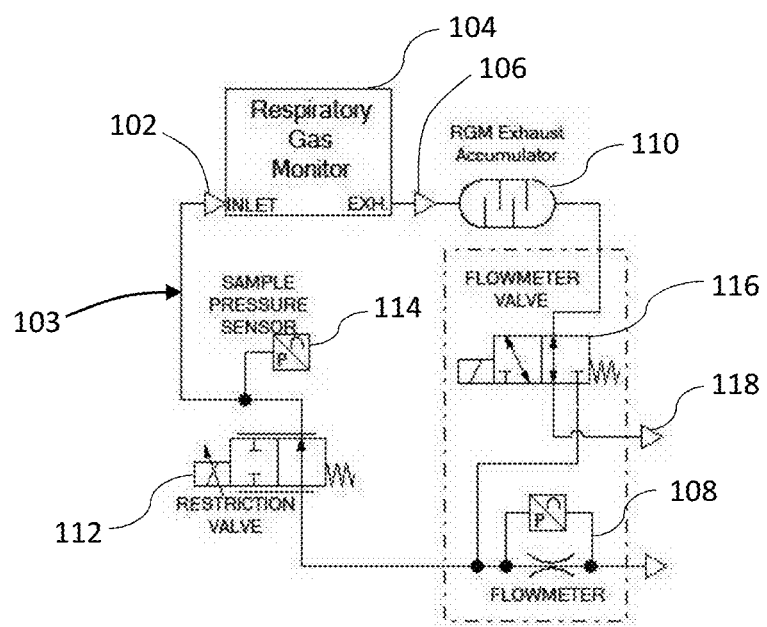
FIG. 1D is a pneumatic schematic of a system for detecting leaks comprising a flowmeter valve which allows the flowmeter to either measure leak or sample flow rate.

In yet another embodiment, as shown in FIG. 1D, a system of detecting the leak rate may also comprise a flowmeter valve 116. The gas sensor in most gas monitors 104 requires a specific sample flow rate to maintain accuracy. It is useful to be able to directly measure the sample flow rate as a diagnostic test of the gas monitor 104. When the flowmeter valve 116 is in its de-energized state, the exhaust 106 from the gas monitor 104 is vented out port 118 and the full sample flow is drawn in through the flowmeter 108, thus allowing the flowmeter 108 to directly measure the sample flow rate. When the flowmeter valve 116 is energized, the exhaust 106 of the gas monitor 104 is placed in fluid communication with the RGM sample line 103 and the flowmeter 108, creating the flow loop, such that the flowmeter 108 is measuring only the leak rate.

In one embodiment, a method for detecting a leak rate comprises measuring the inlet flow rate of the diverting gas monitor, measuring the exhaust flow rate of the diverting gas monitor, and determining the difference in rates to derive the leak rate.

Figure 2A:
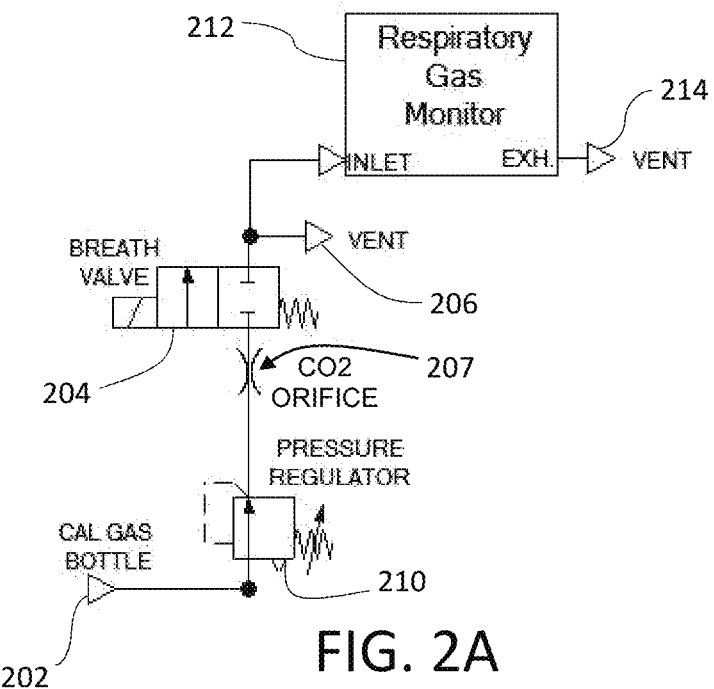
FIG. 2A is a pneumatic schematic of a system of simulating human breath.

Referring now to FIG. 2A, a respiratory gas monitor testing system may comprise a system for simulating human breath. The system for simulating human breath comprises a calibration gas source 202, a valve 204 (the "breath valve") and a vent 206. In this embodiment, calibration gas is forced by a calibration gas source 202 (e.g., cal gas bottle) through the pressure regulator 210 through an orifice 207 to control flow, and to the breath valve 204. When the breath valve 204 is in an energized state (i.e., open), the calibration gas is delivered to the RGM 212, and any excess calibration gas flows out through the vent 206 of the respiratory gas monitor testing system. This simulates the expiratory phase of human breath. When the breath valve 204 is in its de-energized state (i.e., closed) the calibration gas stops flowing and the RGM 212 draws in ambient air through the vent 206, simulating the inspiratory phase of human breath. If the breath valve 204 is cycled (i.e., alternated from energized to de-energized) at regular intervals, the RGM 212 will display a waveform similar to real patient breath. Because this is a simple embodiment, it has the disadvantage of not being capable of higher respiratory rates because it is dependent on the relatively small sampling flow, drawn in by the RGM 212, to flush out the gas of the previous breath phase. In this embodiment, at higher respiratory rates, the air and calibration gas mix, resulting in an inaccurate waveform.

Figure 2B:
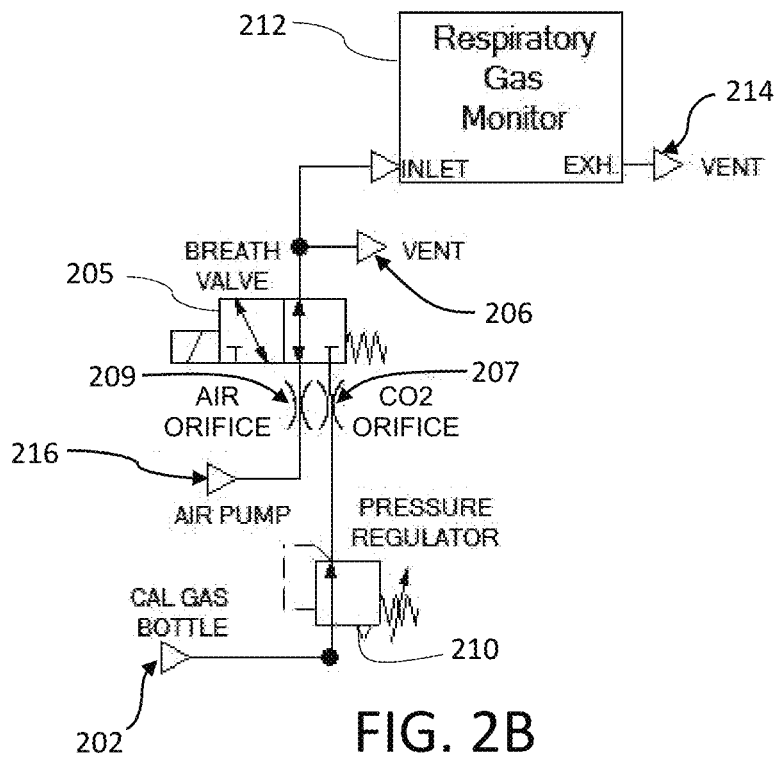
FIG. 2B is a pneumatic schematic of a system of simulating human breath at higher rates using an air pump.

Due to the limitations of the previous embodiment, another embodiment, adapted for simulating human breath at higher respiratory rates, is generally shown at FIG. 2B. This system for simulating human breath at higher respiratory rates comprises a calibration gas source 202, an air source 216 (e.g., an air pump), and a valve 205 (the "breath valve"). This valve can be a multi-port valve as shown in FIG. 2B or a network of simple valves. The internal volume of the valve (or system of valves) should be minimized to reduce the time required to flush the calibration gas out with air, or to flush the air out with calibration gas, thus producing very sharp transitions in gas composition required for simulating high respiratory rates. In this embodiment, calibration gas is forced by a calibration gas source 202 (e.g., cal gas bottle), where it passes through the pressure regulator 210 and orifice 207 (to control flow rate) and to the breath valve 205. When the breath valve 205 is in an energized state, the calibration gas is delivered to the RGM 212. When the breath valve 205 is in a de-energized state, ambient air is delivered to the RGM 212 by the air pump 216, through an orifice 209 (to control flow rate) and to the breath valve. This configuration causes either air or calibration gas to flow constantly out of the vent 206 of the respiratory gas monitor testing system, which serves to flush out the gas from the previous breath phase, allowing for sharp transitions in gas composition (air vs. cal gas), even at higher respiratory rates. It will be appreciated that while the embodiments described herein to control the flow of air and cal gas may incorporate the use of an air pump and air orifice, and a cal gas bottle, pressure regulator, and cal gas orifice, the present invention is not limited to such configurations and other known methods of controlling the flow rate may be used.

Figure 2C:
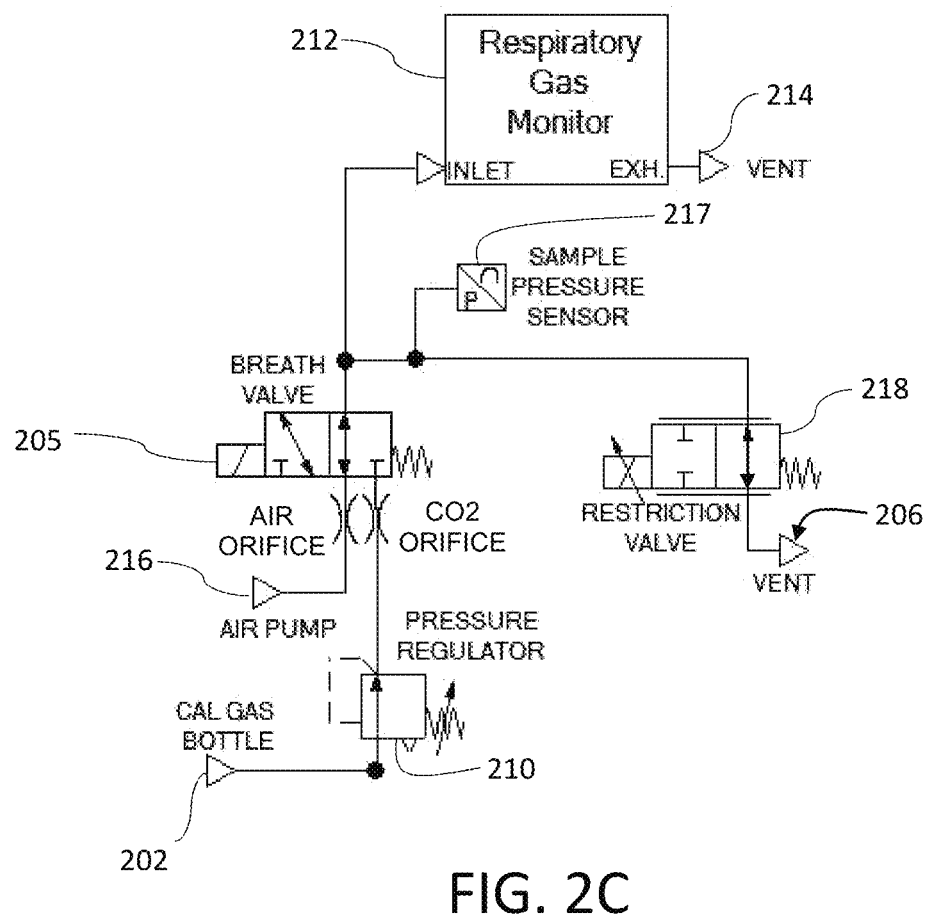
FIG. 2C is a pneumatic schematic of a system of simulating human breath comprising a restriction valve and a pressure sensor to simulate positive airway pressure.

Respiratory gas monitors are commonly used on mechanically ventilated patients. In these circumstances, the sample line of the RGM is subjected to elevated pressures, caused by the mechanical ventilator, required to push air into the patient's lungs. This elevated pressure can cause leaks or other failure modes to exhibit that would not be observed during traditional testing at ambient pressure. In the previous embodiment, generally shown at FIG. 2B, gas (either air or cal gas) is constantly flowing out of the vent 206. Due to the need to simulate elevated pressure on the sampling line of the RGM, another embodiment may be used, which is generally shown at FIG. 2C. In this embodiment, a sample pressure sensor 2167 and variable restriction valve 218 are added to the vent 206. By feedback controlling the variable valve 218 to target a specific pressure at the sample pressure sensor 217, mechanical ventilation pressures can be simulated. Cyclic pressure can be targeted approximating mechanical ventilation. Alternatively, constant pressure can be targeted, to simulate constant positive airway pressure (CPAP).

With the ability to simulate patient breath, the test system can simulate breath for a time, then stop simulating breath to test the apnea alarm of the RGM 212. In addition, with the breath simulation stopped, the restriction valve 218 can be fully energized to completely occlude the sample flow. This allows the user to observe if the occlusion alarm of the RGM 212 is functional.

In one embodiment, a system or method for simulating human breath (e.g., FIG. 2C) may be combined with the system or method for measuring sample flow rate and leak rate (e.g., FIG. 1D) to derive the respiratory gas monitor testing system 300 (see FIG. 3) capable of testing multiple parameters. To integrate the flow and leak measurement system (FIG. 1D) with the patient breath simulation system (FIG. 2C), an additional valve (cal gas valve 322 of FIG. 3) is required to ensure no leakage can occur through the patient breath simulation pneumatics (FIG. 2C) during the portion of the test when the sample flow rate and leak tests are being performed. In this embodiment, the breath simulation portion and the leak/sample flow rate testing portion can share the same sample pressure sensor 312 and restriction valve 314 to reduce battery power consumption, cost and complexity of the test system.

Figure 3:
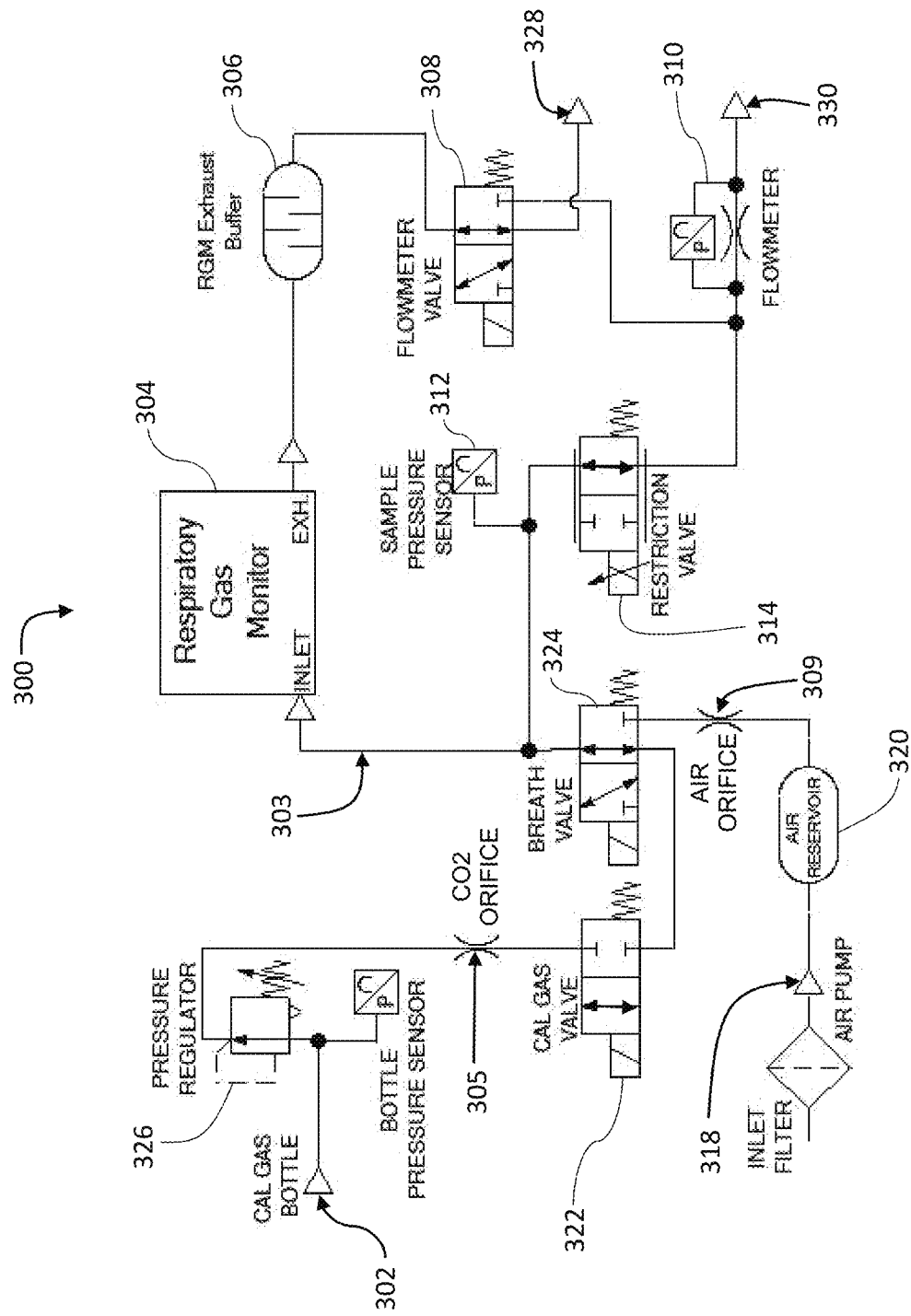
FIG. 3 is a pneumatic schematic of a system for testing respiratory gas monitors that combines a system for detecting leaks with a system of simulating human breath.

In more detail, referring to FIG. 3, a respiratory gas monitor testing system 300 comprises a pressurized gas (the "calibration gas" or "cal gas") source 302, a pressurized air source 318, a respiratory gas monitor 304, a system for detecting the leak rate, and a system for simulating breath. The system for detecting the leak rate comprises at least one valve 308 (the "flowmeter valve"), a flowmeter 310, a sample pressure sensor 312, and a proportional restriction valve 314 (the "restriction valve"). The system for simulating human breath comprises a pressurized air source 318 (e.g., an air pump), and at least two valves: a calibration gas valve (also referred to as a cut-off valve) 322, and a breath simulation valve 324. The valves may be single multi-port valves, as shown in the figures, or a network of simple valves.

In one example embodiment for simulating patient breath, calibration gas is forced by a cal gas source 302, through pressure regulator 326 and to the calibration gas valve 322. As shown, an orifice 305 (or other flow regulator) may also be included to regulate flow. When calibration gas valve 322 is in an energized state, the gas then passes to breath valve 324 which, when in its de-energized state, allows the gas to proceed to the RGM 304. The gas flow delivered by the cal gas bottle 302 is greater than the flow drawn in by the RGM 304, causing the excess flow to pass out through the restriction valve 314 and to vent to atmosphere at outlet 330. The gas that is drawn in by the RGM 304 is exhausted through the buffer 306 into flowmeter valve 308. In its de-energized state, the flowmeter valve 308 then exhausts the gas through outlet 328 to the atmosphere. An air pump 318, or other pressurized air source, forces room air into the air reservoir 320 to pressurize it. While an air reservoir is included here, to reduce pressure spikes from the pump, it is not required. In other words, the pump 318, coupled to the reservoir 320, and further coupled to orifice 309, is an example of one way to drive the air at a predictable flow and pressure. While this configuration is described herein, other configurations that achieve the same means are specifically contemplated herein and such changes will not depart herefrom. For example, a more complex system, such as a mass flow controller, may be employed. Also, a simpler solution may be employed, such as a bottle of compressed air, or a tightly controlled air pump with no reservoir or orifice. When the breath valve 324 is energized, the cal gas flow is stopped and room air from the air reservoir 320 flows through the orifice 309 (to control the flow rate) through the breath valve 324, and to the RGM 304. The air flow is greater than the flow drawn in by the RGM 304 so the excess flow passes through the restriction valve 314 and is vented at outlet 330. The breath valve 324 repeatedly toggles between air from the air source 318 and cal gas from the cal gas source 302 causing the gas composition delivered to the RGM 304 to alternate. This simulates the gas composition that would be drawn in by the RGM 304 if it were connected to a real patient. Because the composition of gas in room air is known and the composition in the cal gas source is known, the RGM 304 can be expected to return a known set of respiratory parameters (end tidal CO2, inspired fraction of CO2, Oxygen concentration, etc). Because the rate at which the breath valve 324 toggles is known and controlled by the system, the RGM 304 can be expected to return a respiratory rate value equal to one-half (½) the breath valve 324 toggle frequency. This allows the user to verify that the RGM 304 is returning accurate values for gas composition and respiratory rate, thus validating the RGM's performance, solving a need in the art.

RGM's are commonly utilized on patients receiving mechanical ventilation. During mechanical ventilation, the ventilator forces the patient to inhale by applying pressure to the patient's airway. The ventilator allows the patient to exhale by venting the patient's airway to atmosphere. In this common circumstance, the sampling line of the RGM is subjected to cyclic positive pressure. This pressure can cause an RGM to exhibit failure modes that would not be observed during normal calibration procedures at ambient pressure. In order to detect these failure modes, the present invention discloses a means to simulate positive pressure while simulating patient breath. Because the flow delivered by the air pump 318 and the calibration gas source 302 is always in excess of the flow drawn in by the RGM 304, there is always flow through the restriction valve 314 that is vented through outlet 330. By continuously restricting this flow using the restriction valve 314, a target sample pressure can be simulated using feedback from the sample pressure sensor 312. This simulated pressure can be constant, simulating constant positive airway pressure (CPAP), or the pressure targeted can by cyclical with the breath, resulting in a pressure waveform that would be observed during mechanical ventilation. This allows the performance of the RGM 304 to be validated under static and dynamic positive pressure, simulating real-world application.

In addition to simulating patient breath, it is essential to detect if the RGM 304 has any leaks internally, or in the sample line that leads from the patient to the RGM 304. Even small leaks can dilute the sample gas, causing the RGM 304 to give false readings. These leaks can be very difficult to detect without extensive training and knowledge of the particular RGM being tested.

In order to test the RGM 304 for leaks, the leak detection systems previously described herein are utilized. The breath valve 324 and the cal gas valve 322 are both left in their de-energized state, preventing any flow from the cal gas source 302 and the air source 318. The flowmeter valve 308 is energized, causing the exhaust flow from the RGM 304 to be put into fluid communication with the sample line 303 of the RGM 304 through the restriction valve 314, creating a flow loop. If there is no leak in the RGM 304 or the sampling line 303, the flow out of the RGM 304 exhaust will be the same as the flow into the sampling line 303, resulting in no net flow in or out of the vent 330. However, if there is any leak inside the RGM 304, a corresponding flow will pass through the flowmeter 310, due to conservation of mass. An exhaust buffer 306 may or may not be used between the exhaust of the RGM 304 and the flowmeter valve 308 to remove the pulsatility (which can make accurate flow measurement difficult) in the flow that exits the RGM 304.

Further, the flow of gas through the sample line 303 may be restricted using restriction valve 314, which exacerbates the leak by creating additional strain/load on the system. This strain creates a greater negative pressure at the inlet of the RGM 304, revealing leaks that only happen at greater negative pressures. For example, most gas monitors are designed to increase the sample pump rate in an effort to maintain a constant flow rate of gas through the system. If the length of the sample line is increased, or humidity or other particle/material enters the sample line, the monitor will compensate to keep the flow rate at its target value, resulting in a more negative pressure in the sampling line. The restriction valve 314 may restrict the flow of gas in order to simulate this effect by targeting a particular negative pressure level during the leak test.

With the breath simulation and leak detection systems integrated (FIG. 3) it is possible to test the RGM for at least each of the following binary characteristics:

Is the sample flow rate in spec at ambient pressure?
Is there a leak detected at ambient pressure?
Does the leak at ambient pressure have a negative value?
Is sample flow not significantly lower under negative pressure load than at ambient?
Is there a leak under negative pressure load (challenge pressure)?
Is the leak at challenge pressure no larger than at ambient pressure?
Is the EtCO2 accurate at ambient pressure?
Is the EtCO2 higher with static positive pressure than at ambient pressure?
Is the EtCO2 either higher or lower with static positive pressure than at ambient pressure?
Is the EtCO2 accurate at the max respiratory rate?
Is the apnea alarm functional?
Is the occlusion alarm functional?

The answers to each of the above questions can be used as the input to a logic table to make one or more diagnosis indicating the most likely cause(s) of the RGM's malfunction. Table 5A-I gives each of the possible diagnosis and the logic required to select a particular diagnosis. For example, if a leak is detected in the sampling system (e.g., the RGM, sampling tube, and associated components), and the leak has a negative value (meaning that gas is being drawn into the sample line instead of expelled), then the system can predict that the leak is on the negative pressure side (upstream) of the sample pump. This is relevant because gas drawn in through a leak acts to dilute the sample gas, causing an inaccurate reading. When the test system applies a positive pressure to the sampling line, it will either reduce or reverse the direction of the leak rate. This will result in less, or zero, dilution of the gas sample. If the leak is located upstream of the gas composition sensor system located within an RGM, the change in dilution will be observed as an increase in the concentration reading (due to less dilution from air drawn in through the leak). On the other hand, if the leak is between the gas composition sensor system and the internal pump of the RGM, the change in pressure will have no effect on the gas reading. This logic allows the system to report to the user the most likely location of the leak as being upstream of the gas composition sensor, between the gas composition sensor and the pump, or downstream of the pump. This feature enables the user to more easily find and repair the leak in the system. Each of the diagnosis in Table 5A-I has a similar logical process to arrive at a specific diagnostic message, which is provided to the user. These messages are shown in the last row under the logic statements of Table 5A-I.

RGMs that are intended to be used on pediatric or neonatal patients need to be capable of gas sensor response times fast enough to give an accurate measurement of end-tidal gas readings, even when the breath rate is very high (80-120 breaths per minute). Each RGM manufacturer publishes the maximum respiratory rate that their RGM is capable of accurately reading. However, many failure modes can cause the response time to be compromised, resulting in inaccurate end-tidal gas readings at high respiratory rates. It is useful, as a means of RGM performance verification, to provide a means to determine if the RGM is capable of meeting its accuracy specifications at the maximum respiratory rate published by the manufacturer. In one embodiment, a method for detecting RGM response time comprises simulating patient breath and monitoring the end-tidal value displayed by the RGM during ascending respiratory rate. For example, the amount of CO2 may be alternated from 0% to 5% repeatedly. The frequency at which the gasses alternate is gradually increased until the gas monitor fails to accurately report the 0% value and/or the 5% value. In other words, as the rate increases, the sensor will eventually fail to transition fast enough, and will instead begin to read a mixture of the two gasses. When a mixed reading given by the RGM falls outside of the stated accuracy specification of the RGM manufacturer, the response time is then known.

Calibration gas can be very expensive, especially if it contains an anesthetic agent. In one embodiment, a method for conserving expensive calibration gas comprises measuring the sample flow rate of the RGM (i.e., by measuring at the flowmeter) and delivering slightly more calibration gas flow than is required by the RGM so that only a minimum flow rate of gas exits the system to the ambient air at the flowmeter vent. Without knowing what sample flow rate is required by a given RGM, a user must input excess calibration gas to the system. However, if the RGM has a relatively low sample flow rate, this can mean that a substantial amount of calibration gas is wasted. If the test system can measure the flow required, and is equipped with means to reduce the calibration gas flow rate accordingly, it can save expensive calibration gas. Control of calibration gas flow can be accomplished by replacing the orifice 305 with a variable valve similar to restriction valve 314.

Figure 4A:
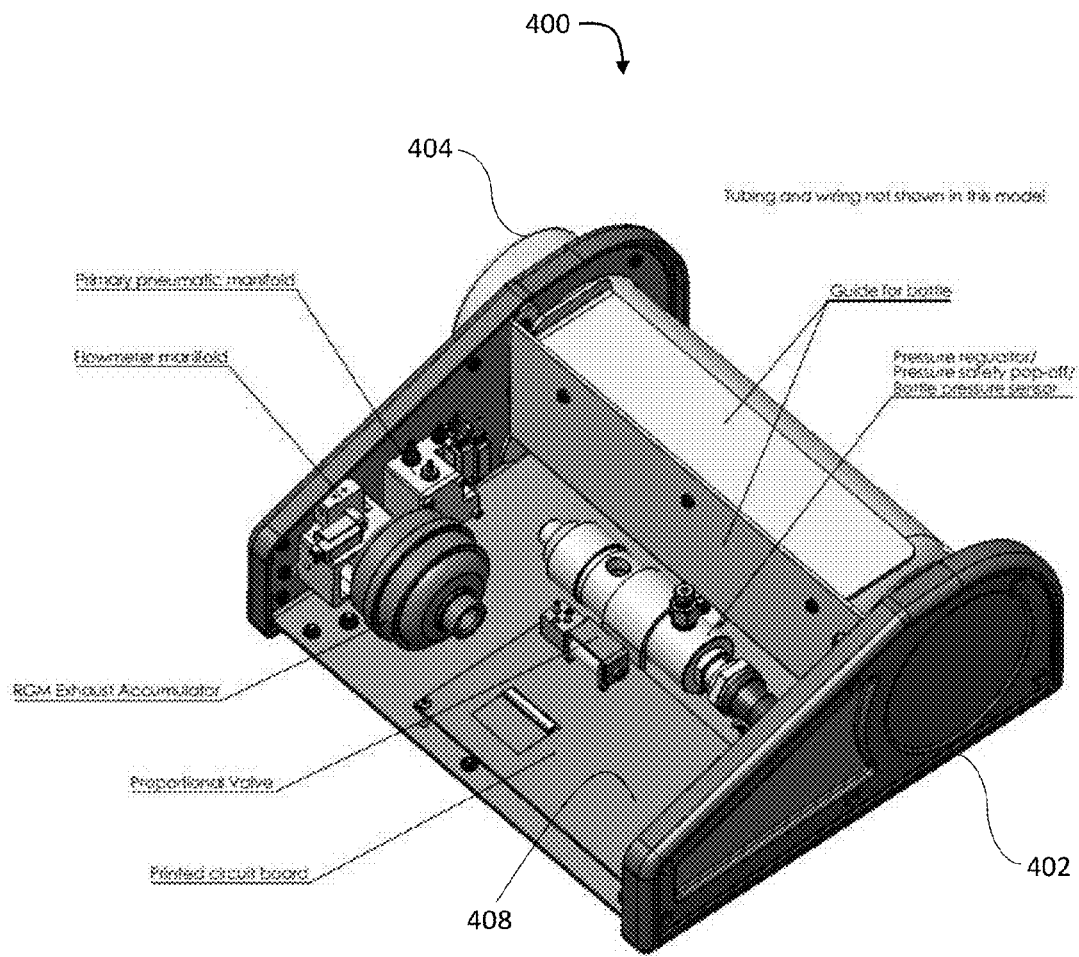
FIG. 4A is a perspective view of a device for detecting leaks and simulating human breath, in one embodiment, with the cover removed.
Figure 4B:
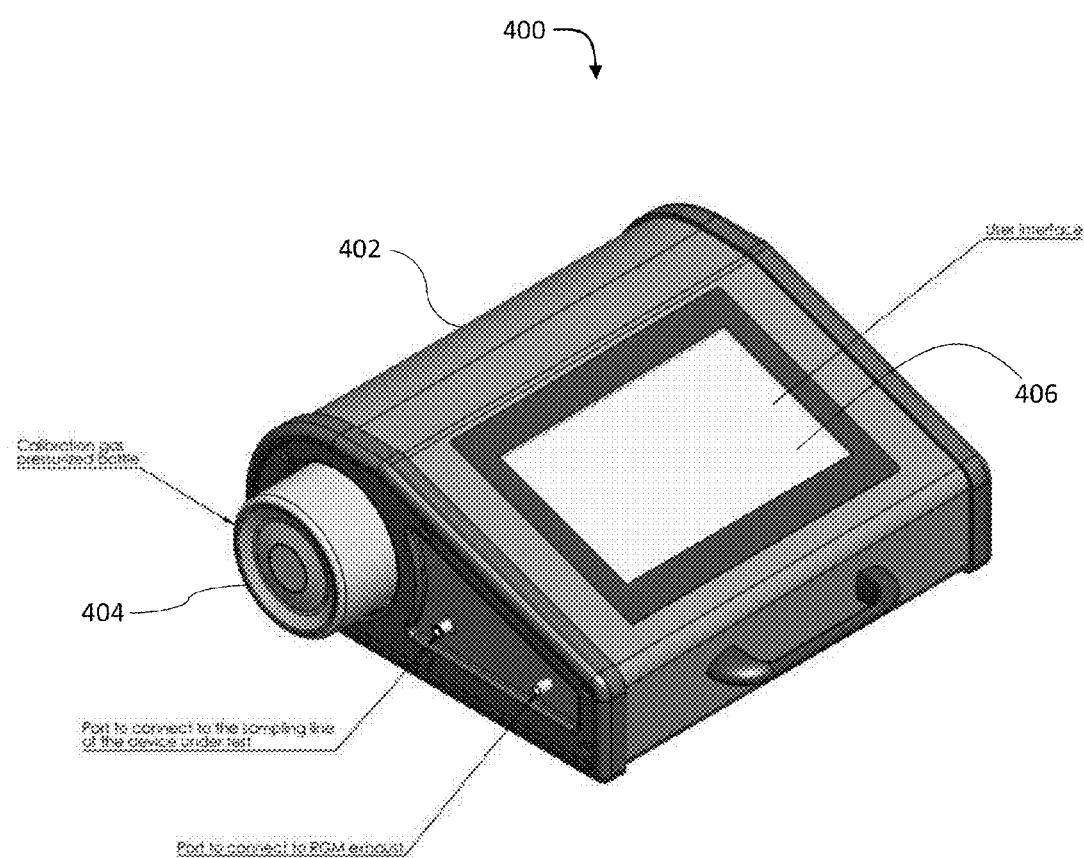
FIG. 4B is a perspective view of a device for detecting leaks and simulating human breath, in one embodiment, with a cover; and Table 5A-I gives each of the possible diagnosis of the system and the logic required to select a particular diagnosis.

As shown in FIGS. 4A and 4B, the systems and methods described above herein may be accomplished using a single testing device 400. As shown, testing device 400 comprises a housing 402, a compressed bottle of calibration gas 404, a user interface 406 (e.g., lcd screen or equivalent), a circuit board 408, and, depending upon the embodiment described above being practiced, the relevant sensors, meters, and valves in accordance with the above embodiments.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention.

What is claimed is:

1. A respiratory gas monitor testing system, comprising: a respiratory gas monitor coupled to a system for detecting a leak, wherein the system for detecting a leak comprises a flowmeter in fluid communication with both an inlet and an outlet of the respiratory gas monitor, with the exhaust of the flowmeter venting to atmosphere.

2. The respiratory gas monitor testing system of claim 1, wherein the system for detecting the leak further comprises a restriction valve.

3. The respiratory gas monitor testing system of claim 1, wherein the system for detecting a leak further comprises a sample pressure sensor.

4. The respiratory gas monitor testing system of claim 1, wherein the system for detecting a leak further comprises a flowmeter valve configured to allow the flowmeter to either measure sample flow rate or leak rate.

5. The respiratory gas monitor testing system of claim 1, wherein the system for detecting a leak further comprises a flow-smoothing buffer configured to improve flow measurement accuracy.

6. The respiratory gas monitor testing system of claim 1, further comprising a system for simulating human breath.

7. The respiratory gas monitor testing system of claim 6, wherein the system for simulating human breath comprises an air source, a calibration gas source, and a breath simulation valve.

8. The respiratory gas monitor testing system of claim 7, wherein the system for simulating human breath further comprises a calibration gas valve.

9. The respiratory gas monitor testing system of claim 7, wherein the system for simulating human breath further comprises a sample pressure sensor.

10. The respiratory gas monitor testing system of claim 7, wherein the system for simulating human breath further comprises an air reservoir.

11. The respiratory gas monitor testing system of claim 7, wherein the calibration gas source comprises a pressurized bottle with a pressure regulator and an orifice.

12. The respiratory gas monitor testing system of claim 7, wherein the air source comprises an air pump.

13. A method of using a respiratory gas monitor testing system to determine a leak rate, comprising:
 creating a gas flow loop by placing an inlet of a gas monitor in fluid communication with the exhaust of the gas monitor;
 connecting an inlet of a flowmeter to the gas flow loop and allowing the exhaust of the flowmeter to vent to atmosphere; and
 monitoring the flow of gas in or out of the vent through the flowmeter.

14. The method of using a respiratory gas monitor testing system of claim 13, further comprising using a buffer chamber between the respiratory gas monitor exhaust and the flowmeter to smooth the flow of gas.

15. The method of using a respiratory gas monitor testing system of claim 13, further comprising using a restriction valve to vary the inlet pressure of the respiratory gas monitor.

16. The method of using a respiratory gas monitor testing system of claim 15, further comprising using a pressure sensor to monitor the pressure caused by the restriction valve.

17. The method of using a respiratory gas monitor testing system of claim 13, further comprising using a valve to select if the flowmeter is measuring sample flow rate or leak rate.

18. A respiratory gas monitor testing system, comprising:
 a system of simulating patient breath, comprising:
  (a) inputting calibration gas through a pressure regulator and to a breath valve;
  (b) the breath valve configured to alternate between an open and closed state;
  (c) wherein if the breath valve is open, the calibration gas flows to a respiratory gas monitor;
  (d) wherein if the breath valve is closed, the calibration gas flow is stopped and ambient air enters from an air source, the ambient air flowing to the respiratory gas monitor; and
  (e) a vent positioned between the breath valve and the respiratory gas monitor configured to vent to atmosphere excess gas flow from the breath valve that is not drawn in by the respiratory gas monitor.

19. The respiratory gas monitor testing system of claim 18, further comprising a restriction valve and a sample pressure sensor on the vent configured to simulate positive airway pressure.

20. A method of determining proper functionality of a respiratory gas monitor using the respiratory gas monitor testing system of claim 18, comprising:
 comparing a composition of gas in ambient air and a composition of gas in a calibration gas source, corrected for barometric pressure, with respiratory parameters output by the respiratory gas monitor.

21. A method of using a respiratory gas monitor testing system to determine a leak rate in a diverting gas monitor, comprising:
 measuring an inlet flow rate of the diverting gas monitor, measuring an exhaust flow rate of the diverting gas monitor, and determining a difference in rates to derive the leak rate.

22. A respiratory gas monitor testing method, comprising:
 simulating patient breath and detecting a leak, wherein simulating patient breath comprises:
  (a) inputting calibration gas through a pressure regulator and to a calibration gas cut-off valve; an outlet of the calibration gas cut-off valve leading to a breath valve;
  (b) inputting air from an air source to the breath valve;
  (c) the breath valve configured to alternate between a de-energized and energized state;
  (d) wherein if the calibration gas cut-off valve is energized and the breath valve is de-energized, the calibration gas flows to a respiratory gas monitor;
  (e) wherein if the breath valve is energized, the calibration gas flow is stopped and ambient air enters from the air source, the ambient air flowing to the respiratory gas monitor;
  (f) a vent positioned between the breath valve and the respiratory gas monitor configured to vent to atmosphere excess gas flow from the breath valve that is not drawn in by the respiratory gas monitor;
  (g) a variable restriction valve positioned on a vent line to control pressure in a respiratory gas monitor sample line;
  (h) a sample pressure sensor positioned on the vent line between the respiratory gas monitor sample line and the variable restriction valve such that pressure caused by the variable restriction valve can be measured; and
  (i) a flowmeter positioned on the end of the vent line downstream of
 the restriction valve, and venting to atmosphere; and
 wherein detecting a leak comprises:
  (a) a flowmeter valve configured to vent an exhaust of the respiratory gas monitor to atmosphere when de-energized and further configured to place the exhaust of the respiratory gas monitor in fluid communication with the flowmeter, restriction valve, sample pressure sensor, and sample line of the system of simulating patient breath, creating a flow loop; and
  (b) wherein if a leak is present, measuring a leak rate using the flowmeter.

23. A method of using a respiratory gas monitor testing system to diagnose a malfunction of a respiratory gas monitor, comprising the steps of:
 (a) coupling the respiratory gas monitor to the respiratory gas monitor testing system, wherein the respiratory gas monitor testing system comprises the logic as described in Table 5A-5I; and
 (b) diagnosing the malfunction of the respiratory gas monitor according to the logic.

* * * * *